(12) United States Patent
Paul et al.

(10) Patent No.: US 6,344,183 B2
(45) Date of Patent: *Feb. 5, 2002

(54) AEROSOL HAIR COSMETIC COMPOSITIONS CONTAINING NON-IONICALLY DERIVATIZED STARCHES

(75) Inventors: Charles W. Paul, Madison, NJ (US); Matthew J. Henley, Greenwood, IN (US); Paul A. Altieri, Belle Mead, NJ (US); Melissa J. Vitale, Plainsboro, NJ (US); Maria Tolchinsky, Monmouth Junction, NJ (US); Daniel B. Solarek, Belle Mead, NJ (US); Ian W. Cottrell, Princeton, NJ (US)

(73) Assignee: National Starch and Chemical Investment Holding Corporation, New Castle, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/280,614

(22) Filed: Mar. 29, 1999

Related U.S. Application Data

(63) Continuation-in-part of application No. 09/057,717, filed on Apr. 9, 1998, now abandoned.

(51) Int. Cl.$^7$ .................................................. A61K 7/11
(52) U.S. Cl. ..................... 424/47; 424/45; 424/70.11; 424/70.13; 424/70.15; 424/70.16; 424/DIG. 1; 424/DIG. 2
(58) Field of Search ............................. 424/70.11, 70.13, 424/70.15, 70.16, 45, 47, DIG. 1, DIG. 2

(56) References Cited

U.S. PATENT DOCUMENTS

| | | | |
|---|---|---|---|
| 3,186,911 A | 6/1965 | Rieger et al. .............. 167/87.1 |
| 3,479,427 A | 11/1969 | Lieberman et al. ........... 424/47 |
| 3,507,290 A | 4/1970 | Halleck ......................... 132/7 |
| 3,697,644 A | 10/1972 | Laiderman ................... 424/70 |
| 3,715,428 A | 2/1973 | Quasius et al. ................ 424/47 |
| 3,790,664 A | 2/1974 | Krochock et al. ............ 424/47 |
| 4,059,458 A | 11/1977 | Germino et al. ............ 106/213 |
| 4,283,384 A | 8/1981 | Jacquet et al. ................ 424/47 |
| 4,328,319 A | 5/1982 | Osipow et al. ............... 521/78 |
| 4,364,837 A | 12/1982 | Pader ......................... 252/173 |
| 4,411,891 A | 10/1983 | Mizutani et al. ............ 424/180 |
| 4,638,822 A | 1/1987 | Grollier et al. ................ 132/7 |
| 4,663,159 A | 5/1987 | Brode et al. .................. 424/70 |
| 4,734,478 A | 3/1988 | Tsubakimoto et al. ....... 527/300 |
| 4,913,743 A | 4/1990 | Brode et al. ................ 106/162 |
| 5,030,443 A | 7/1991 | Varco et al. ................... 424/47 |
| 5,124,446 A | 6/1992 | Gruning et al. ............. 536/120 |
| 5,126,126 A * | 6/1992 | Varaprath et al. |
| 5,449,763 A | 9/1995 | Wulff et al. ................ 536/18.6 |
| 5,482,704 A | 1/1996 | Sweger et al. ........... 424/70.13 |
| 5,871,756 A * | 2/1999 | Jeffcoat et al. |

FOREIGN PATENT DOCUMENTS

| | | | |
|---|---|---|---|
| EP | 0 149 249 | 7/1985 | ......... C08B/11/145 |
| EP | 0 487 000 | 5/1992 | ............ A61K/7/48 |
| GB | 1285547 | 8/1972 | ............ C08B/19/04 |
| JP | 54-011108 | 1/1979 | ............ C11D/3/37 |
| JP | 55-45602 | 3/1980 | ............ A61K/7/00 |
| JP | 61210008 A | 9/1986 | ............ A61K/7/00 |
| WO | 98/01109 | 1/1998 | ............ A61K/7/48 |

* cited by examiner

Primary Examiner—Raj Bawa
(74) Attorney, Agent, or Firm—Karen G. Kaiser

(57) ABSTRACT

The present invention is directed to low volatile organic compound aerosol hair cosmetic compositions which contain nonionically derivatized starches optionally hydrolyzed and/or ionically modified, about 5–55% propellant, up to 50% solvent, and water. Such compositions provide a clear solution with a low viscosity, good spray caracteristics, a clear, non-tacky film, good stiffness, and improved humidity resistance.

31 Claims, No Drawings

AEROSOL HAIR COSMETIC COMPOSITIONS CONTAINING NON-IONICALLY DERIVATIZED STARCHES

This application is a continuation-in-part of U.S. Ser. No. 09/057,717 filed Apr. 9, 1998 now abandoned.

BACKGROUND OF THE INVENTION

The present invention relates to novel aerosol hair cosmetic compositions, particularly hair fixative compositions, which contain nonionically derivatized starches and to a process for setting hair utilizing such compositions.

In their most basic form, hair cosmetic compositions contain a film-forming polymer, which acts as the cosmetic, and a delivery system, which is usually one or more alcohols, a mixture of alcohol and water, or water. In the case of aerosol delivery, the delivery system will also contain a propellant, typically a volatile hydrocarbon.

The hair setting or styling process ordinarily involves the application of an aqueous solution or dispersion of one or more film-forming materials to combed hair which has previously been wettened or dampened whereupon the treated hair is wound on curlers or otherwise styled and dried. In the alternative, application of this solution or dispersion may be to hair which has already been styled and dried. Once the aqueous solution or dispersion has dried, the individual hairs will have a film deposited thereon which presence will prolong the retention of curls or other desired configurations in the user's hair. Furthermore, the presence of such films will impart such desirable properties as body and smoothness.

To be effective, the film-forming ingredients of a hair cosmetic composition preferably meet a number of requirements. The film derived from these ingredients should be flexible, yet possess strength and elasticity. The ingredients should display good adhesion to hair so as to avoid dusting or flaking off with the passage of time or when the hair is subjected to stress; should not interfere with the combing and brushing of the hair; should remain free of tack or gumminess under humid conditions; should be clear, transparent, and glossy, and should maintain clarity upon aging. Further, the ingredients should maintain good antistatic properties and should be easily removable by washing with water and either a soap or shampoo.

Many film-forming agents have been used in hair cosmetic compositions including, for example, a colloidal solution containing a gum such as tragacanth or a resin such as shellac. The films formed of these materials are, however, quite brittle and the form holding the setting is easily broken if the hair is disturbed. This not only reduces the hair holding power of the material, but also leads to undesirable flaking. Further, some of these film-formers, particularly the resins, are water insoluble and therefore not easily removed with water and soap or shampoo.

Starches are often preferred over resins as they are more cost effective and natural. Hair cosmetic compositions which contain starches are also known in the art. For example, GB 1,285,547 discloses a hair setting composition containing a highly substituted cationic starch having an amylose content of more than 50% by weight. EP 487 000 discloses cosmetic compositions which contain enzymatically degraded optionally crosslinked starches. However, such derivatives are not significantly soluble in water.

Due to environmental regulations controlling the emission of volatile organic compounds (VOCs) into the atmosphere, VOC emissions have been restricted to 80% in some states, and will soon be restricted to 55% in California. VOC is measured as a wt/wt% based upon the hair cosmetic formulation. As used herein, a volatile organic compound containing from 1 to 10 carbon atoms, which has a vapor pressure of at least 0.1 mm Hg at 20° C., and is photochemically active. Water is generally substituted for at least a portion of the volatile organic compounds and so has become a greater component in hair cosmetic compositions.

Many fixatives, particularly starches, are incompatible with water in that they are not fully soluble, resulting in starch precipitates which may clog aerosol valves and produce poor spray aesthetics. Further, many starch fixatives are also incompatible with propellant. Surprisingly, it has now been discovered that nonionically derivatized starches are useful in aerosol hair cosmetic compositions with low volatile organic compounds in that they provide a clear solution with a low viscosity, good spray aesthetics, improved humidity resistance, and good fixative properties.

SUMMARY OF THE INVENTION

The present invention is directed to low volatile organic compound aerosol hair cosmetic compositions which contain nonionically derivatized, particularly propylene oxide derivatized, starches. Derivatized, as used herein, is intended to mean chemically modified via a reagent. The nonionically derivatized starch may be further hydrolyzed, particularly enzymatically hydrolyzed by at least one endo-enzyme. In addition, the nonionically derivatized starch may be ionically modified, particularly by octenyl succinic anhydride (OSA). Use of such starches is novel and advantageous in that they provide a clear solution with a low viscosity, and good spray characteristics. Further, the resultant composition provides a clear film which is not tacky, has good hold, and improved humidity resistance.

The present hair cosmetic composition contains by weight from about 0.5 to about 15% of the instant starch, from about 5 to about 55% of a propellant, from zero to about 50% of a solvent, and sufficient water to bring the composition up to 100%.

An object of this invention is to provide a novel hair cosmetic composition which contains nonionically derivatized starches and low volatile organic compounds.

Another object of this invention is to provide a novel hair cosmetic composition which contains nonionically derivatized starches which have been hydrolyzed.

Still another object of this invention is to provide a novel hair cosmetic composition which contains starches which have been derivatized with propylene oxide and enzymatically hydrolyzed.

Yet another object of this invention is to provide a novel hair cosmetic composition which contains starches which have been nonionically derivatized, hydrolyzed, and ionically modified.

A further object of this invention is to provide a novel hair cosmetic composition which contains starches which have been derivatized with propylene oxide, enzymatically hydrolyzed and modified with octenyl succinic anhydride.

A still further object of this invention is to provide a novel hair cosmetic composition which has improved humidity resistance, superior stability and contains low volatile organic compounds.

A yet further object of this invention is to provide a novel hair cosmetic composition which contains starch which has been derivatized and coprocessed with polyvinyl pyrrolidone.

These and other objects of the present invention will become apparent to one skilled in the art from the following detailed description and examples below.

DETAILED DESCRIPTION OF THE INVENTION

The present invention is directed to aerosol hair cosmetic compositions, i.e., hair sprays, which contain nonionically derivatized starches, particularly propylene oxide derivatized starches, in a low or no volatile organic compound (hereinafter VOC) solution, particularly less than 55% VOC, most particularly less than 35% VOC, by weight of the hair setting composition. The starch may be additionally hydrolyzed, particularly enzymatically hydrolyzed. Further, the starch may be modified using ionic substituents. Use of such starches is novel and advantageous in that they provide a clear solution with a low viscosity, and good spray characteristics. Further, the resultant composition provides a clear film which is not tacky and good curl retention.

The hair cosmetic composition of the instant invention contains a fixative effective amount of a nonionically derivatized starch, particularly from about 0.5 to about 15% starch, more particularly from about 2 to about 10% by weight; from about 5 to about 55% of a propellant, particularly from about 5 to about 40%, from zero to about 50% of a solvent, particularly from about 5 to about 35% by weight; and sufficient water to bring the composition to 100%.

All starches and flours (hereinafter "starch") are suitable for use herein and may be derived from any native source. A native starch or flour as used herein, is one as it is found in nature. Also suitable are starches and flours derived from a plant obtained by standard breeding techniques including crossbreeding, translocation, inversion, transformation or any other method of gene or chromosome engineering to include variations thereof. In addition, starch or flours derived from a plant grown from artificial mutations and variations of the above generic composition which may be produced by known standard methods of mutation breeding are also suitable herein. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof. As used herein, the term "waxy" is intended to include a starch or flour containing at least about 95% by weight amylopectin and the term "high amylose" is intended to include a starch or flour containing at least about 45% by weight amylose.

The starch is first nonionically derivatized using an ester or ether which is compatible with the system, particularly with the solvent and the propellant. Methods of nonionic derivatization are well known in the art and may be found for example in *Starch Chemistry and Technology*, 2nd ed., Edited by Whistler, et al., Academic Press, Inc., Orlando (1984) or *Modified Starches: Properties and Uses*, Wurzburg, O. B., CRC Press, Inc., Florida, (1986).

Nonionic reagents include, but are not limited to alkylene oxides such as ethylene oxide, propylene oxide, and butylene oxide, acetic anhydride, and butyl ketene dimer. Particularly suitable nonionic reagents are the alkylene oxides, more particularly propylene oxide. The nonionic reagent is added in an amount of from about 1 to 50%, particularly from about 5 to 25%, more particularly from about 7.5 to 18%.

For example, the starch may be derivatized using propylene oxide as follows. An aqueous starch slurry containing from about 5 to about 40%, particularly 30 to 40%, solids is prepared. From about 20 to about 30% percent sodium sulfate based on the weight of the starch is added. The pH is then adjusted to about 11 to about 13 by addition of a 3% sodium hydroxide solution in an amount of from about 40 to about 60% based upon the weight of the starch. The desired amount of propylene oxide is added. The temperature is brought to the range of about 35 to 50° C., particularly about 40° C., and the process is allowed to continue for about 18 to about 24 hours.

The starch is generally at least partially gelatinized. If conversion is to be accomplished enzymatically, the gelatinization is conventionally conducted prior to conversion. Gelatinization may be accomplished using any technique known in the art, particularly steam cooking, more particularly jet-cooking, and then converted (hydrolyzed). The conversion is important if a reduced molecular weight starch and a reduced viscosity of the starch solution or dispersion is desired, such as when the starch is to be used in a hair spray. The conversion may be accomplished by any method known in the art, such as by enzymes, acid, dextrinization, man-ox, or oxidation, particularly by enzymes. If conversion is conducted using acid or oxidation methods, then it may be done prior to or after derivatization of the starch.

The enzymatic hydrolysis of the starch is carried out using techniques known in the art. Any enzyme or combination of enzymes, known to degrade starch may be used, particularly endo-enzymes. Enzymes useful in the present application include, but are not limited to, α-amylase, β-amylase, maltogenase, glucoamylase, pullulanase, particularly α-amylase and pullulanase. The amount of enzyme used is dependent upon the enzyme source and activity, base material used, and the amount of hydrolysis desired. Typically, the enzyme is used in an amount of from about 0.01 to about 1.0%, particularly from about 0.01 to 0.3%, by weight of the starch.

The optimum parameters for enzyme activity will vary depending upon the enzyme used. The rate of enzyme degradation depends upon factors known in the art, including the enzyme concentration, substrate concentration, pH, temperature, the presence or absence of inhibitors, and the degree and type of modification. These parameters may be adjusted to optimize the digestion rate of the starch base.

Generally the enzyme treatment is carried out in an aqueous or buffered slurry at a starch solids level of about 10 to about 40%, depending upon the base starch being treated. A solids level of from about 15 to 35% is particularly useful, from about 18 to 25% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 22 to about 65° C. is used, particularly from about 50 to about 62° C. In general, the pH is adjusted to about 3.5 to about 7.5, particularly from about 4.0 to about 6.0, using techniques known in the art.

In general, the enzyme reaction will take from about 0.5 to about 24 hours, particularly about 0.5 to about 4 hours.

The time of the reaction is dependent upon the type of starch used, the amount of enzyme used, and the reaction parameters of solids percent, pH, and temperature.

The enzyme degradation is then terminated by any technique known in the art such as acid or base deactivation, heat deactivation, ion exchange, and solvent extraction. For example, acid deactivation may be accomplished by adjusting the pH to lower than 2.0 for at least 30 minutes or heat deactivation may be accomplished by raising the temperature to about 85 to about 95° C. and maintaining it at that temperature for at least about 10 minutes to fully deactivate the enzyme. Heat deactivation is not suitable if a granular product is desired as the heat necessary to deactivate the enzyme will generally also gelatinize the starch.

The conversion reaction is continued until the starch is sufficiently degraded to provide proper spray characteristics, particularly to a viscosity of from about 7 to about 80 seconds, more particularly from about 10 to about 60 seconds, measured at 19% w/w solid concentration at room temperature using a standard funnel method. The resultant product may be further characterized by a dextrose equivalent (DE) of from about 2 to about 40 and/or a water fluidity of from about 60 to 80.

Funnel viscosity, as used herein, is defined by the following procedure. The starch dispersion to be tested is adjusted to 19% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air and the balance is poured back into the funnel. The graduated cylinder in then inverted over the funnel so that the contents draw (flow) into the funnel while the sample is running. Using a timer, the time required for the 100 ml sample to flow through the apex of the funnel is recorded.

The glass portion of the funnel is a standard 58°, thick-wall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip which is about 5.08 cm long with an outside diameter of about 0.9525 cm. The interior diameter of the steel tip is about 0.5952 cm at the upper end where is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

Finally, the starch may be ionically modified, either anionically, cationically, or zwitterionically. Starch modification techniques are known in the art and may be found, for example, in *Starch Chemistry and Technology*, 2nd ed., Edited by Whistler, et al., Academic Press, Inc., Orlando (1984) or *Modified Starches: Properties and Uses*, Wurzburg, O. B., CRC Press, Inc., Florida, (1986).

Anionic modification may be accomplished by any reagent known in the art, such as alkenyl succinic anhydrides, inorganic phosphates, sulfates, phosphonates, sulfonates, and sodium chloroacetic acids. Particularly suitable anionic reagents are alkyenyl succinic anhydrides and sodium chloroacetic acids, more particularly octenyl succinic anhydride.

Modification of starch using octenyl succinic anhydride may be accomplished by reacting the selected starch with sufficient octenyl succinic anhydride reagent such that the resulting starch is sufficiently soluble or dispersible in the water or water solvent delivery system. In particular, the starch will be modified to have a degree of substitution from about 0.2 to about 3.0, preferably from about 0.3 to about 1.6. The degree of substitution (DS) is used herein to describe the number of ester substituted groups per anhydroglucose unit of the starch molecule.

Cationic modification must be to a low degree of substitution, particularly less than about 0.3 equivalents per 100 grams starch. The cationic modification may be accomplished by any reagent known in the art including those containing amino, imino, ammonium, sulfonium, or phosphonium groups. Such cationic derivatives include those with nitrogen containing groups comprising primary, secondary, tertiary and quaternary amines and sulfonium and phosphonium groups attached through either ether or ester linkages. Cationic modification, particularly tertiary amino or quaternary ammonium etherification of starch, typically prepared by treatment with 3-chloro-2-hydroxypropyltrimethyl ammonium chloride, 2-diethylaminoethyl chloride, epoxypropyl trimethylammonium chloride, 3-chloro-2-hydroxypropyldimethyl dodecyl ammonium chloride, and 4-chloro-2-butenyltrimethylammonium chloride.

Zwitterionic modification may be accomplished using any reagents known in the art, such as N-(2-chloroethyl)-iminobis(methylene)diphosphonic acid and 2-chloroethylaminodipropionic acid (CEPA).

In general, the degree of nonionic derivatization desired will be greater when the starch is not ionically modified than when the starch is ionically modified.

Optionally, the starch may then be neutralized by raising the pH of the solution to from about 5 to about 9. This may be done by any method known in the art, particularly by the addition of amino methyl propanol sodium hydroxide, potassium hydroxide, or other bases know in the art.

The starch solution is generally filtered to remove impurities, particularly fragmented starch. Filtration may be accomplished by any technique known in the art, particularly by filtration through diatomaceous earth.

The starch may be used as a solution or may be recovered in powdered form by conventional techniques, such as drum-drying or spray-drying.

The modified starch may further be blended or coprocessed with other fixative or conditioning polymers. Such polymer may be selected from polymers known in the art, such as vinyl acetate/crotonates/vinyl neodecanoate copolymer, octylacrylamide/acrylates/butylaminoethyl methacrylate copolymer, vinyl acetate/crotonates, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates copolymer, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/ methacryloamidopropyl trimethylammonium chloride terpolymer, methacrylates/acrylates copolymer/amine salt, polyvinylcaprolactam, polyurethanes, polyquaternium-4, polyquaternium-10, polyquaternium-11, polyquaternium46, hydroxypropyl guar, hydroxypropyl guar hydroxypropyl trimmonium chloride, polyvinyl formamide, polyquaternium-7, and hydroxypropyl trimmonium chloride guar particularly polyvinyl pyrrolidone.

To coprocess the starch and the polymer, the polymer is dissolved in water. The modified starch is then slurried into the dispersed polymer and the slurry is processed. Processing includes cooking and drying, particularly jet cooking and spray drying, and includes the methods disclosed in U.S. Pat. Nos. 5,149,799; 4,280,851; 5,188,674 and 5,571,552 incorporated herein by reference.

The delivery system in most cases will be a blend of water and one or more volatile organic compounds acting as solvents. The amount of solvent will be present in an amount of from zero to about 50%, particularly from about 5 to about 35% by weight of the composition. However, it is possible to prepare hair cosmetic compositions containing the present starches in which the delivery system comprises primarily water or even essentially no solvent.

Typically, the organic solvent will be a lower alcohol (herein defined as an alcohol having from 1 to 7 carbon atoms), particularly methanol, ethanol, propanol, isopropanol, or butanol. Also suitable are acetals, esters, and ketones, particularly dimethoxymethane and acetone.

A propellant is added to formulate the aerosol hair cosmetic composition. Propellants useful in the instant invention include, but are not limited to, ethers, such as dimethyl ether; one or more lower boiling hydrocarbons such as $C_3$–$C_6$ straight and branched chain hydrocarbons, for example, propane, butane, and isobutane; halogenated hydrocarbons, such as, hydrofluorocarbons, for example, 1,1-difluoroethane and 1,1,1,2-tetrafluoroethane, present as a liquefied gas; and the compressed gases, for example, nitrogen, air and carbon dioxide.

The amount of propellant used in the hair cosmetic compositions of this invention may vary from about 5 to about 55%, particularly from about 5 to about 40% by weight of the hair cosmetic composition. It should be noted that the above propellants are volatile organic compounds. However, the emission of halogenated hydrocarbons such as hydrofluorocarbons, and the compressed gases are not at this time subject to environmental regulations; therefore, these compounds may be formulated into the hair sprays of this invention without inclusion in the total VOC content.

Optional conventional additives may also be incorporated into the hair spray compositions of this invention to provide certain modifying properties to the composition. Included among these additives are plasticizers, such as glycerine, glycol and phthalate esters; emollients, lubricants and penetrants, such as lanolin compounds; fragrances and perfumes; UV absorbers; dyes and other colorants; thickeners; anticorrosion agents; detackifying agents; combing aids and conditioning agents; antistatic agents; neutralizers; glossifiers; preservatives; foam stabilizers; emulsifiers; and surfactants. Such additives are commonly used in hair cosmetic compositions known heretofore. These additives are present in small, effective amounts to accomplish their function, and generally will comprise from about 0.1 to 10% by weight each, and from about 0.1 to 20% by weight total, based on the weight of the composition.

The instant starch-containing hair care compositions may also be combined with other modified or unmodified starches that provide added functional benefits. For example, formulations with 2-chloroethylamino dipropionic acid derivatives of potato starch or hydroxypropyl starch phosphate may be incorporated for thickening or rheology modification in hair styling lotions and creams, and starches such as tapioca starch, corn starch, aluminum starch octenyl succinate, or corn starch modified may be used in the hair care compositions as aesthetic enhancers to provide silkier, smoother formulations. Modified starches, as used herein, is intended to include without limitation, converted starches, cross-linked starches, acetylated and organically esterified starches, hydroxypropylated and hydroxyethylated starches, phosphorylated and inorganically esterified starches, cationically, anionically or zwitterionically modified starches, and succinated and substituted succinated starches. Such modified starches are known in the art for example in *Modified Starches: Properties and Uses* by Wurzburg. Particularly suitable modified starches include hydroxypropylated starches, octenyl succinate derivatives, and 2-chloroethylamino dipropionic acid derivatives.

To prepare the aerosol hair cosmetic composition, a solution of the starch in the water or water/solvent mixture is prepared. Then any optional additives may be added.

The mixture is then pressurized with propellant according to conventional standards known in the art to form the aerosol hair cosmetic composition. Pressures utilized are those conventionally used to prepare aerosol sprays, such as from about 30 psi to about 110 psi.

Hair cosmetic compositions include, but are not limited to, hair fixative compositions and styling aids, such as hair sprays and mousses.

One advantage of the instant starch-containing hair care compositions is that the starches are substantially soluble in water and compatible with the propellant. This allows a reduced solvent or a substantially solvent-free composition to be formulated. Solubility is important in that the presence of particulate matter (i.e., undissolved starch) may clog the valve actuators, interfering with delivery of the composition by aerosol.

Another advantage of the instant compositions is that they are of relatively low viscosity. This helps to eliminate the undesirable stickiness and heaviness associated with many conventional hair cosmetic compositions.

A further advantage of the instant hair cosmetic compositions is that they do not become tacky at high relative humidity (RH), unlike many conventional water-based starch-containing hair cosmetic compositions.

The present starches may also be used in skin, oral, and other hair care applications, such as lotions, creams, sun screens, lip balms, tanning products, oral rinses, antiperspirants, shampoos, and conditioners.

The following examples are presented to further illustrate and explain the present invention and should not be taken as limiting in any regard.

EXAMPLES

All percentages in the examples are calculated on a wt/wt basis. The following test procedures are used throughout the examples.

A. Determination of the High Humidity Curl Retention of Hair Sprays

The curl retention properties of the hair spray starches are measured at 72° F. /90% Relative Humidity over a period of 24 hours.

Equipment

8" Remi Blue String European Brown hair

Barber shears

Nylon comb

White Cotton thread (size #8)

3"×½" Teflon mandrels

Forced air oven@ 120° F.

Plexiglass retention board

Environmental chamber (precision to ±2 R.H. @ 72° F.)

Prell Shampoo

Procedure

Preparation of Curl Swatches

1. Separate hair into small swatches of approximately 2 grams in weight.
2. Secure hair sample ¾" from root end by winding with cotton thread.
3. Fold over at root end and secure the hair into a small loop with thread. Leave approximately 6" of loose thread to secure identification tag.
4. In order to prevent loss of individual hair shafts during combing, glue the root end at the thread windings with epoxy cement. Allow cement to harden.
5. Wash hair swatch in a 10% solution of shampoo. Then rinse thoroughly with warm tap water.
6. Comb to untangle the hair shafts.
7. Cut the hair swatch to measure 6" in length from the looped root end. Dry @ 120° F.

Preparation and Exposure of Test Samples

1. Wet hair and comb through to remove snarls.
2. Squeeze-out excess water by running the swatch between thumb and index finger.
3. Curl hair into a coil configuration by rolling it on a ½" diameter Teflon mandrel. Secure hair on mandrel with plastic clips.
4. Dry hair, mandrel and clip 120° F.
5. When hair is dry and cool, carefully remove clips and hair curl from the mandrel.
6. Suspend the hair curl from the bound end. Apply a controlled amount of hair spray in a controlled manner. In evaluating an aerosol hair spray, a 2. second "burst" is evenly applied to both the from and back of the curl from a distance of 6".
7. Lay the freshly sprayed curl on a horizontal surface and allow to air dry for 1 hour.
8. Suspend the dry curls in random fashion from graduated, clear, transparent, plexiglass curl retention boards.
9. Take initial curl height reading ($L_o$) and set curl retention boards into the environmental chamber.
10. Record curl length ($L_t$) at the 15, 30, 60 and 90 minute, 2, 3, 4, 5 and 24 hour intervals.

Calculations

Calculate percentage curl retention by:

$$\text{Curl Retention \%} = L - L_t/L - L_o \times 100$$

Where:

L=length of hair fully extended $L_o$=length of hair before exposure $L_t$=length of hair after exposure B. Initial Curl Droop Scope Initial curl droop (ICD) is defined as the immediate loss of curl integrity upon spraying a suspended, dry curl with a water-containing formulation.

Equipment

6" Brown hair (9 rolled swatches per sample)

Plexiglass retention board

Digital timers or stop watches

Procedure

1. Determine both spray rate and polymer deposition of each aerosol sample prior to testing.
2. Roll swatches onto white Teflon mandrels.
3. Let rolled hair cool and equilibrate at 50% RH, 72° F. for at least three hours before removing from the mandrel.
4. Suspend the hair curl from the bound end onto the retention board using the attached clip. Make sure that the bottom of the curl is lined up with the "0" mark on the board.
5. Spray the first side of the curled hair from left to right for the time period specified to maintain uniform polymer deposition by tracking total spray time. Pivot the curl 180 degrees using the clip and complete the spraying cycle on the other side before rotating back to the original position. All spraying should be done from a distance of six inches (nozzle to hair).
6. Record the curl length after 30, 60 and 90 seconds, as well as 2, 4, and 6 minutes following initial spraying, using markings on board.
7. In order to run more than one curl at a time, begin to spray a second curl after the first curl has been tracked for 2–4 minutes. Using another timer, repeat the procedure as described above. Be careful not to allow over spray to contact initial curl. Repeat this process once initial curl has been tracked for 6 minutes.

Results

Calculate percent curl retention for each time interval.

C. Taber Stiffness Test Procedure

Aerosol hair spray formulations are tested for stiffness on three 4¼" swatches of brown European virgin hair and the results pooled and averaged. The swatches are first dried in an oven at 110° F. for 30 minutes to remove moisture and then dried in a desiccator for 15 minutes. The swatches are weighed and the weight recorded as $W_1$. Each swatch is sprayed with a hair spray formulation for one second and then clipped to a retention board and dried in a 110° F. oven for 15 minutes. The swatches are cooled in the desiccator and reweighed. This weight was recorded as $W_2$. The swatches are then placed to equilibrate overnight at 50% relative humidity and 23° C.

Stiffness is tested using a Taber V-5 Stiffness Tester from Taber Industries of North Tonawanda, N.Y., designed for evaluating stiffness and resilience of paper, cardboard, and other flexible materials. The following procedure and calculation are used with hair samples.

When the machine is first turned on, the optical encoder inside the unit is oriented and the pendulum balanced according to manufacture's instructions.

The hair swatch is inserted between the clamp jaws, with the lower edge resting lightly on the bottom gauge. The clamp jaws are tightened by turning the screws on either side of the clamp.

The swatch is centered between the bottom rollers. With one finger, apply light pressure to the control lever switch and deflect the driving disc to the left until the line on the pendulum is under the 15° deflection mark. Use a smooth, continuous motion without abrupt starts and stops.

Record the stiffness reading on the outer scale that falls opposite to the zero line on the driving disc (LS). Now deflect the same swatch to the right by 15° and take that stiffness reading (RS). Average the left and right readings and multiply by five. The product is the stiffness value for that swatch.

D. Removability Test Procedure

Using aerosol formulas, spray eight hair swatches with experimental formulation and eight with control formulation and allow to dry at ambient conditions for one hour. For each swatch, rinse under tap water for 1 minute while working fingers into hair. Put wet swatches in 110° F. oven until dry.

Pair off experimental swatches vs. control swatches, and evaluate subjectively for residual stiffness, flake, and feel properties.

E. Tack and Drying Time Test Procedure

Suspend eight sets of two untreated hair swatches, each separately. Spray one swatch of each set with experimental formulation and other swatch with control formulation simultaneously. Immediately feel swatches for tack and drying times. Record time that tack starts, tack ends, and when each swatch feels dry. Subtract tack start time from tack end time to obtain total tack time.

Example 1

Preparation of Starch Modified with Propylene Oxide a. A 40% aqueous solution of waxy starch was prepared and 25% sodium sulfate was added. The pH was then adjusted to about 11.5 uses a 3% sodium hydroxide solution. The starch was treated with 7.5% propylene oxide. The pH was then adjusted to 5.5 using dilute sulfuric acid.

b. Example 1a was repeated using a propylene oxide level of 15%.

c. Example 1a was repeated using a propylene oxide level of 3%.

d. Example 1a was repeated using a 50% amylose corn starch.

e. Example 1a was repeated using a 70% amylose corn starch.

f. Example 1b was repeated using tapioca starch.

g. Example 1b was repeated using potato starch.

Example 2

Preparation of Hydrolyzed Starch Modified with Propylene Oxide a. The slurried starch of Example 1a was adjusted to a pH of 5.5 using sulfuric acid and cooked until fully gelatinized. The starch was then hydrolyzed using α-amylase to a funnel viscosity of about 30 seconds.

b. Example 2a was repeated using a 70% amylose starch.

c. Example 2a was repeated hydrolyzing to a funnel viscosity of 10 seconds.

d. Example 2a was repeated hydrolyzing to a funnel viscosity of 60 seconds.

Example 3

Preparation of Hydrolyzed Starch Modified with Propylene Oxide and Octenyl Succinic Anhydride a. A 40% aqueous slurry of Amioca™ starch was prepared. 25% sodium sulfate was added. The pH was then adjusted to about 11.50 by addition of a 3% sodium hydroxide solution. The starch was then treated with propylene oxide at a level of 7.5%. After reaction the pH was adjusted to 3.5 using sulfuric acid. The solution was allowed to stir for one hour and the pH was then adjusted to 5.5 with 3% sodium hydroxide. Next the starch was cooked until fully gelatinized and hydrolyzed with alpha-amylase to a funnel viscosity of 30 seconds. The starch cook was cooled to room temperature. Octenyl succinic anhydride was then added at a level of 6% while maintaining the pH at 7.5 using 25% sodium hydroxide solution. The starch was allowed to react until caustic consumption stopped. The pH was then adjusted to 5.5 using dilute hydrochloric acid solution. The starch was then filtered through Celite (Celite 512 is a diatomaceous earth commercially available from Celite Corporation).

b. Example 3a was repeated using propylene oxide at a level of 15%.

c. Example 3a was repeated using propylene oxide at a level of 3%.

d. Example 3a was repeated hydrolyzing the starch to a funnel viscosity of less than 10 seconds.

e. Example 3a was repeated hydrolyzing the starch to a funnel viscosity of 15 seconds.

f. Example 3a was repeated hydrolyzing the starch to a funnel viscosity of 60 seconds.

g. Example 3a was repeated hydrolyzing the starch using concentrated hydrochloric acid for sixteen hours and then neutralizing by addition of sodium carbonate and sodium hydroxide.

h. Example 3a was repeated hydrolyzing the starch by using sodium hypochlorite solution for sixteen hours. 10% sodium bisulfite solution was added to remove residual hypochlorite and neutralized using dilute hydrochloric acid.

i. Example 3a was repeated using potato starch in place of Amioca.

Example 4

Preparation of Other Modified Hydrolyzed Starches a. A 40% aqueous slurry of Amioca™ starch was prepared. The pH was adjusted to about 11.5 using 3% NaOH. The slurry was treated with 5% 3-chloro-2-hydroxypropyltrimethyl ammonium chloride. The slurry was allowed to react for 10–12 hours while maintaining pH=1 1.5 using 3% NaOH. The starch was then adjusted to pH=5.5 using dilute hydrochloric acid solution, filtered and washed. Next the starch was cooked until fully gelatinized and hydrolyzed with alpha-amylase to a funnel viscosity of 30 seconds. The starch cook was cooled to room temperature. Octenyl succinic anhydride was then added at a level of 6%. The pH was maintained at 7.5 using 25% sodium hydroxide solution. The starch was allowed to react until caustic consumption stopped. The pH was then adjusted to 5.5 using dilute hydrochloric acid solution. The starch was then filtered through Celite (Celite 512 is a diatomaceous earth commercially available from Celite Corporation).

b. Example 4a was repeated using 3-chloro-2-hydroxypropyltrimethyl ammonium chloride at a level of 10%.

c. Example 4a was repeated substituting the use of 2-chloroethylaminodiproprionic acid at a level of 5% for the use of 3-chloro-2-hydroxypropyltrimethyl.

d. A 40% aqueous slurry of Amioca™ starch was prepared. 25% sodium sulfate was added. The pH was then adjusted to about 11.50 by addition of a 3% sodium hydroxide solution. The starch was then treated with propylene oxide at a level of 7.5%. After reaction the pH was adjusted to 3.5 using sulfuric acid. The solution was allowed to stir for one hour and the pH was then adjusted to 5.5 with 3% sodium hydroxide. Next the starch was cooked until fully gelatinized and hydrolyzed with alpha-amylase to a funnel viscosity of 30 seconds. The starch cook was cooled to room temperature. Acetic anhydride was added at a level of 7.5%, while maintaining the slurry pH=7.5 with 25% NaOH. The starch was allowed to react until caustic consumption stopped. The pH was then adjusted to 5.5 using dilute hydrochloric acid solution. The starch was then filtered through Celite (Celite 512 is a diatomaceous earth commercially available from Celite Corporation).

e. A 40% aqueous slurry of Amioca™ starch was prepared. 25% sodium sulfate was added. The pH was then adjusted to about 11.50 by addition of a 3% sodium hydroxide solution. The starch was then treated with propylene oxide at a level of 7.5%. After reaction the pH was adjusted to 3.5 using sulfuric acid. The solution was allowed to stir for one hour and the pH was adjusted to 5.5 with 3% sodium hydroxide. Next the starch was cooked until fully gelatinized and hydrolyzed with alpha-amylase to a funnel viscosity of 30 seconds. The starch cook was cooled to room temperature. Acetic anhydride was added at a level of 7.5%, while maintaining the slurry pH=7.5 with 25% NaOH. Octenyl succinic anhydride was then added at a level of 6%, maintaining pH=7.5 using 25% NaOH. The starch was allowed to react until caustic consumption stopped. The pH was then adjusted to 5.5 using dilute hydrochloric acid solution. The starch was then filtered through Celite (Celite 512 is a diatomaceous earth commercially available from Celite Corporation).

Example 5

Coprocessing of Starch with a Polymer 5 g of polyvinyl pyrrolidone (PVP) were dissolved in 900 grams of water. 100 g of the starch of example 1e is then slurried into the polymer solution. The slurry was jet cooked at 150–155° C. and then conveyed under pressure directly to the spray drier to prevent retrogradation. The cooked slurry was spray dried with an inlet temperature of 230° C. and an outlet temperature of 120° C.

Example 6

Neutralization of the Starch

The starches of examples 1–5 were neutralized by the addition of 2-amino 2-methyl 1-propanol.

Example 7

Preparation of Hair Spray Solution a) The starches of examples 1–6 were each made into a hair spray solution using the following method. The starch was diluted with water to a 7.5% solids solution. Dimethyl ether propellant was added to made the final concentration 5% starch, 33% propellant, and 62% water.

Example 8

Performance of Starches in an Aerosol Hair Spray

The starches from Examples 3a and 3b were formulated into low VOC aerosol hair spray systems according to the following formulations. All values reported are parts by weight, based on the total weight of the hair spray composition.

| Ingredient | Parts by Weight (dry basis) Alcohol-free (33% VOC) |
|---|---|
| starch polymer | 5.0 |
| deionized water | 62.0 |
| dimethyl ether | 33.0 |

With agitation, the starch polymer is sifted into deionized water until homogeneous. Solutions were filtered and filled into aerosol containers. Cans were charged with dimethyl ether propellant. Hair spray formulations were tested for spray characteristics on 2 gram swatches of European brown hair. The sprays were delivered with a Seaquist NS-34 valve (0.013" vapor tap×0.013" stem orifice×0.040" dip tube diameter) having an Excel 200 Misty (0.016" orifice) actuator in a 2 second burst from a distance of six inches. Formulas were compared to:

Control A (diglycol/CHDM/isophthalates/SIP copolymer in a 5% solids, 33% VOC aerosol, commercially available from Eastman Chemical Company, Kingsport, Tenn.);

Control B (VA/crotonates/vinyl neodecanoate copolymer in a 5% solids, anhydrous aerosol commercially available from National Starch and Chemical Company, Bridgewater, N.J.);

Control C (acrylates/octylacrylamide copolymer in a 5% solids, anhydrous aerosol commercially available from National Starch and Chemical Company, Bridgewater, N.J.); and/or Control D (octylacrylamide/acrylates/ butylaminoethyl methacrylate copolymer in a 5% solids anhydrous aerosol commercially available from National Starch and Chemical Company, Bridgewater, N.J.).

| Ingredient | Anhydrous Formulations Parts by Weight (dry basis) |
|---|---|
| polymer | 5.0 |
| 2-amino-2-methyl-1-propanol (AMP)[a] | 1.0 |
| anhydrous ethanol | 69.0 |
| A-46 hydrocarbon[b] | 25.0 |

[a] commercially available from Angus Chemical Company
[b] isobutane/propane

Aerosol Solubility

The solubility of the starches in the hair spray composition are determined by checking clarity immediately after formulation and after 12 hours. The results are shown in Table I below.

TABLE I

| Starch ↓ | Initial | After 12 hours |
|---|---|---|
| Example 3a | clear | slightly hazy |
| Example 3b | clear | clear |

Spray Characteristics

The spray characteristics of the alcohol-free aerosols were rated on a scale from A to F, with A being the best spray. An "A" rating indicates a wide spray cone, fine spray, small particle size, and no foam on the hair or actuator. An "F" rating indicates a narrow spray cone, spitting at the actuator, large particle size, and obvious foaming on the hair or actuator. Mean particle size of the sprays were measured by a Malvern Series 2600 Droplet and Particle Size Analyzer from Malvern Instruments Inc. of Southborough, Mass. The results are listed in Table II.

TABLE II

| Polymer | % VOC Aerosol | Mean Particle Size (μ) | Spray Rating |
|---|---|---|---|
| Example 3a | 33 | 33.92 | B |
| Example 3b | 33 | 30.97 | B |

High Humidity (90%) Curl Retention

Mean retention values of nine samples are listed in Table III, below.

TABLE III

| Polymer | 15 min. | 30 min. | 60 min. | 90 min. | 2 hr. | 3 hr. | 4 hr. | 5 hr. | 24 hr. |
|---|---|---|---|---|---|---|---|---|---|
| Example 3a | 95.5 | 91.8 | 89.5 | 88.8 | 86.6 | 85.0 | 84.3 | 84.3 | 80.5 |
| Example 3b | 94.0 | 90.8 | 89.2 | 86.2 | 83.9 | 82.2 | 78.4 | 78.4 | 67.9 |
| Control A | 95.6 | 92.0 | 89.0 | 87.6 | 84.0 | 80.4 | 80.4 | 80.4 | 70.4 |
| Control B | 90.7 | 85.4 | 78.1 | 73.3 | 73.0 | 70.2 | 69.1 | 65.7 | 53.9 |
| Control D | 97.9 | 96.6 | 93.1 | 93.1 | 92.5 | 91.2 | 91.2 | 91.2 | 90.5 |

All of the starch examples are comparable in humidity resistance with the controls.

Shampoo Removability Evaluations

Shampoo removability compared to Control C is listed in Table IV, bellow.

TABLE IV

| Polymer | Stiffness | Flake |
|---|---|---|
| Example 3a | = | = |

Results are statistically equivalent to the control.

Taber Stiffness

TABLE V

| Polymer | % of Control D Stiffness |
|---|---|
| Example 3a | 65% |
| Control A | 72% |

Tack and Drying Time

Tack and drying time was compared to Control D.

TABLE VI

| Polymer | Total Tack Time | Drying Time |
|---|---|---|
| Example 3a | + | + |

Example 3a is statistically superior (less tack, quicker drying time) than the control.

Initial Curl Droop

The compositions were tested at 50% relative humidity (RH). Mean % curl retention values of nine values per sample are shown in Table X below.

TABLE VII

| Starch ↓ | 30 sec | 60 sec. | 90 sec | 2 min | 4 min | 6 min |
|---|---|---|---|---|---|---|
| Example 3a | 93.46 | 91.98 | 91.98 | 88.42 | 86.99 | 84.76 |

Example 9-Evaluation of Starch/Polymer in Mousse

| Ingredient | Amount (g) |
|---|---|
| Polymer | 3.00 |
| Tergitol NP-9 Surfactant[a] | 0.60 |
| Dowicil 200[b] | 0.20 |
| Water | 88.20 |
| Propellant A-46[c] | 8.00 |

[a]Nonoxynol-9 commercially available from Union Carbide
[b]Quaternium-15 commercially available from Dow Chemical Co.
[c]Isobutane/Propane The polymer was slowly dispersed into the water with agitation. The Tergitol and Dowicil were added with continued agitation. The resultant solution was filtered and used to fill aerosol cans. The cans were charged with the propellant.

Polymers

Starch of Example 5

Luviskol VA 64 (PVP/VA 60/40), commercially available from BASF Gafquat, commercially available from International Specialty Products 50:50 blend of Example 5:Gafquat Wet combability and feel The mousse was dispensed onto a wet swatch of hair and combed. Both the wet combability and feel of the formulation using the starch of example 5 were equivalent to that of the Luviskol.

Both the wet combability and feel of the formulation using the 50:50 blend example 5: Gafquat were equivalent to that of the Gafquat alone.

Subjective stiffness

The starch of example 5 provided more stiffness than that of Luviskol. The mousse was then reformulated using 2.25% and 1.5% starch of example 5, using water to substitute for the removed starch. The comparison with Luviskol (at 3%) is shown below.

3% Example 5 stiffer than Luviskol
2.25% Example 5 equivalent stiffness to Luviskol
1.5% Example 5 less stiff than Luviskol The stiffness of the 50:50 blend, Example 5:Gufquat was equal to that of the Gafquat.

| Polymer | Mean Retention (%) |
|---|---|
| Example 5 | 43.49 |
| Gafquat | 36.84 |
| Luviskol | 15.57 |

Example 10

Preparation of All-Natural Texturizing Fixative Lotion

| Ingredients | % By Weight |
|---|---|
| Phase A: | |
| Deionized Water | 55.85 |
| (1) Potato Starch Modified | 1.75 |
| (2) Brij 78 | 2.00 |
| Phase B: | |
| (3) DC 345 | 7.50 |
| (4) DC 200 | 2.50 |
| Phase C: | |
| (5) Lanette O | 1.40 |
| (6) Germall II | 1.00 |
| Phase D: | |
| Propylene Glycol | 5.00 |
| Example 1e | 3.00 |
| Phase E: | |
| Deionized Water | 20.00 |
| | 100.00 |

INCI Designations:
(1) Potato Starch Modified (National Starch and Chemical)
(2) Steareth-20 (ICI Surfactants)
(3) Cyclomethicone (Dow Corning)
(4) Dimethicone (Dow Corning)
(5) Cetearyl Alcohol (Henkel)
(6) Diazolidinyl Urea (Sutton Labs)

Procedure

Potato starch modified was added to cold water and mixed for 2 minutes. The starch solution as heated to 80° C. with mixing at moderate speed. Mixing was continued for 25 minutes at 80° C. Brij 78 was added and mixed until dissolved. Phase B was premixed and added to Phase A under high speed (8,000–10,000 RPM). Lanette O was then added at 80° C. and mixed, followed by addition of Germall II. Phase D was premixed and then Phase E was added to Phase D and mixed well. Phase DE was added to Phase ABC and mixing was continued for approximately 10–15 minutes.

We claim:

1. A hair cosmetic composition comprising:
   a) a fixative effective amount of a nonionically modified starch, wherein the starch is chemically modified using a reagent selected from the group consisting of alkylene oxide, acetic anhydride, and butyl ketene dimer;
   b) an effective amount of a conditioning polymer or a second fixative polymer,
   c) from about 5 to about 55% of a propellant;
   d) up to about 50% solvent: and
   e) water,
   wherein said starch and said polymer (b) are slurried together, cooked and dried.

2. The composition of claim 1, wherein the starch is present in an amount of from about 0.5 to 15% by weight of the composition.

3. The composition of claim 1, wherein the starch is present in an amount of about 2 to 10% by weight of the composition.

4. The composition of claim 1, wherein the starch is a waxy starch.

5. The composition of claim 1, wherein the starch is a high amylose starch.

6. The composition of claim 1, wherein the starch is chemically modified using from about 1 to about 50% of the reagent.

7. The composition of claim 6, wherein the starch is chemically modified using from about 5 to about 25% of the reagent.

8. The composition of claim 1, wherein the starch is nonionically modified using an alkylene oxide.

9. The composition of claim 8, wherein the starch is nonionically modified using propylene oxide.

10. The composition of claim 1, where the starch at a 19% w/w solid concentration at room temperature is further hydrolyzed to a funnel viscosity of from about 7 to about 80 seconds.

11. The composition of claim 1, wherein the starch is further anionically or zwitterionically modified.

12. The composition of claim 1, wherein the starch is further cationically modified at a level of less than about 0.03 equivalents per 100 grams starch.

13. The composition of claim 11, wherein the starch is anionically modified using a reagent selected from the group consisting of alkenyl succinic anhydrides, inorganic phosphates, sulfates, phosphonates, sulfonates, and sodium chloroacetic acids.

14. The composition of claim 13, wherein the starch is anionically modified using the reagent octenyl succinic anhydride.

15. The composition of claim 11, wherein the starch is zwitterionically modified using a reagent selected from the group consisting of N-(2-chloroethyl)-iminobis(methylene) diphosphonic acid and 2-cloroethylaminodipropionic acid.

16. The composition of claim 12, wherein the starch is cationically modified using a reagent containing a group selected from the group consisting of amino, Imino, ammonium, sulfonium, and phosphonium.

17. The composition of claim 16, wherein the starch is cationically modified using a reagent selected from the group consisting of 3-chloro-2-hydroxypropyltrimethly ammonium chloride, 2-diethylaminoethyl chloride, epoxypropyltrimethylammonium chloride and 4-chloro-2-butenyltrimethylammonium chloride.

18. The composition of claim 1, wherein the polymer is selected from the group consisting of vinyl acetate/crotonates/vinyl neodecanoate copolymer, octylacrylamide/acrylates/butylaminoethyl methacrylate copolymer, vinyl acetate/crotonates, polyvinylpyrrolidone (PVP), polyvinylpyrrolidone/vinyl acetate copolymer, PVP acrylates copolymer, vinyl acetate/crotonic acid/vinyl proprionate, acrylates/acrylamide, acrylates/octylacrylamide, acrylates copolymer, acrylates/hydroxyacrylates copolymer, and alkyl esters of polyvinylmethylether/maleic anhydride, diglycol/cyclohexanedimethanol/isophthalates/sulfoisophthalates copolymer, vinyl acetate/butyl maleate and isobornyl acrylate copolymer, vinylcaprolactam/PVP/dimethylaminoethyl methacrylate, vinyl acetate/alkylmaleate half ester/N-substituted acrylamide terpolymers, vinyl caprolactam/vinylpyrrolidone/methacryloamidopropyl trimethylammonium chloride terpolymer, methacrylates/acrylates copolymer/amine salt, polyvinylcaprolactam, polyurethanes, polyquaternium-4, polyquaternium-10, polyquaternium-11, polyquaternium-46, hydroxypropyl guar, hydroxypropyl guar hydroxypropyl trimmonium chloride, polyvinyl formamide, polyquarternium-7, and hydroxypropyl trimmonium chloride guar.

19. The composition of claim 18, wherein the polymer is polyvinyl pyrrolidone.

20. A hair cosmetic composition comprising:
 a) a fixative effective amount of a propylene oxide modified high amylose starch
 b) polyvinyl pyrrolidone (PVP);
 c) from about 5 to about 55% of a propellant;
 d) up to about 50% of a solvent: and
 e) water;
 wherein said starch and said PVP are slurried together, cooked and dried.

21. The composition of claim 1, wherein the composition is substantially solvent-free.

22. The composition of claim 20, wherein the composition is substantially solvent-free.

23. The composition of claim 1, further comprising at least one additional modified or unmodified starch.

24. The composition of claim 23, wherein the additional starch is selected from the group consisting of hydroxypropylated starches, starch octenylsuccinates, and starch 2-chloroethylamino dipropionic acids.

25. The composition of claim 20, further comprising at least one additional modified or unmodified starch.

26. The composition of claim 25, wherein the additional starch is selected from the group consisting of hydroxypropylated starches, starch octenylsuccinates, and starch 2-chloroethylamino dipropionic acids.

27. A method of styling hair comprising applying to the hair the composition of claim 1.

28. A method of styling hair comprising applying to the hair the composition of claim 20.

29. A method of styling hair comprising applying to the hair the composition of claim 21.

30. A method of styling hair comprising applying to the hair the composition of claim 22.

31. A hair cosmetic composition comprising:
 a) fixative effective amount of a propylene oxide modified high amylose starch;
 b) a cellulose polymer chosen from the group consisting of polyquaternium-4, polyquaternium-7, polyquaternium-10, polyquaternium-1.1 and polyquaternium-46;
 c) from about 5 to about 55% of a propellant;
 d) up to about 50% of a solvent; and
 e) water;
 wherein the starch and polymer are slurried together, jet cooked and spray dried.

* * * * *